(12) United States Patent
Moloy

(10) Patent No.: US 11,967,407 B2
(45) Date of Patent: Apr. 23, 2024

(54) METHOD OF ADJUSTING MEDICATION DOSES

(71) Applicant: Sanofi, Paris (FR)

(72) Inventor: Timothy Moloy, Cambridge, MA (US)

(73) Assignee: Sanofi, Paris (FR)

( * ) Notice: Subject to any disclaimer, the term of this patent is extended or adjusted under 35 U.S.C. 154(b) by 556 days.

(21) Appl. No.: 17/262,595

(22) PCT Filed: Jul. 23, 2019

(86) PCT No.: PCT/US2019/042974
§ 371 (c)(1),
(2) Date: Jan. 22, 2021

(87) PCT Pub. No.: WO2020/023473
PCT Pub. Date: Jan. 30, 2020

(65) Prior Publication Data
US 2021/0350892 A1  Nov. 11, 2021

Related U.S. Application Data

(60) Provisional application No. 62/703,740, filed on Jul. 26, 2018.

(30) Foreign Application Priority Data

May 15, 2019 (EP) .................................... 19305621

(51) Int. Cl.
*G16H 20/13* (2018.01)
*A61B 5/00* (2006.01)
(Continued)

(52) U.S. Cl.
CPC ......... *G16H 20/13* (2018.01); *A61B 5/14532* (2013.01); *A61B 5/4839* (2013.01); *A61M 5/1723* (2013.01); *A61M 2230/201* (2013.01)

(58) Field of Classification Search
CPC ........ G16H 20/13; G16H 20/17; G16H 40/63; A61B 5/14532; A61B 5/4839;
(Continued)

(56) References Cited

U.S. PATENT DOCUMENTS 10,772,503 B2 *  9/2020  Raisoni ................ A61B 5/0022
10,925,522 B2 *  2/2021  Chang .................. A61B 5/0022
(Continued)

FOREIGN PATENT DOCUMENTS

CN  102088898 A  6/2011
CN  102369031 A  3/2012
(Continued)

OTHER PUBLICATIONS

PCT International Preliminary Report on Patentability in International Application No. PCT/US2019/042974, dated Jan. 26, 2021, 8 pages.
(Continued)

*Primary Examiner* — Jason S Tiedeman
(74) *Attorney, Agent, or Firm* — Fish & Richardson P.C.

(57) ABSTRACT

Method, apparatus and system for adjusting medicament doses. A method of providing a medication dose adjustment using a computing device comprises: receiving an adjustment cycle time period; receiving a threshold number of dose and blood glucose measurement pairs, the threshold number of dose and blood glucose measurement pairs being less than a total number of potential dose and blood glucose measurement pairs possible in the adjustment time cycle period; receiving a dose and blood glucose measurement pair; determining if a total number of dose and blood glucose measurement pairs received within a current adjustment cycle time period meets the threshold number, the current adjustment cycle time period depending on the received adjustment cycle time period; in response to a positive
(Continued)

determination, determining if a dose adjustment is required based on the dose and blood glucose measurement pairs received within an adjustment cycle time period; and outputting the dose adjustment.

20 Claims, 6 Drawing Sheets

(51) Int. Cl.
*A61B 5/145* (2006.01)
*A61M 5/172* (2006.01)

(58) Field of Classification Search
CPC .............. A61B 5/4842; A61M 5/1723; A61M 2230/201; A61M 2205/3561
USPC ........................................................ 705/2, 3
See application file for complete search history.

(56) References Cited

U.S. PATENT DOCUMENTS

| | | | |
|---|---|---|---|
| 2009/0240127 A1* | 9/2009 | Ray | G16H 40/63 600/300 |
| 2010/0016700 A1* | 1/2010 | Sieh | G16H 15/00 726/16 |
| 2010/0198314 A1* | 8/2010 | Wei | G16H 20/17 702/22 |
| 2010/0256047 A1* | 10/2010 | Sieh | A61P 3/10 702/19 |
| 2010/0332142 A1* | 12/2010 | Shadforth | A61B 5/4833 600/300 |
| 2011/0015511 A1 | 1/2011 | Bousamra et al. | |
| 2011/0238324 A1 | 9/2011 | Matsushima et al. | |
| 2012/0065894 A1 | 3/2012 | Tubb et al. | |
| 2012/0116196 A1* | 5/2012 | Tubb | G16H 20/10 600/365 |
| 2012/0173161 A1* | 7/2012 | Virkamaki | G16H 40/63 702/21 |
| 2012/0179017 A1 | 7/2012 | Satou et al. | |
| 2012/0232520 A1 | 9/2012 | Sloan et al. | |
| 2012/0253840 A1* | 10/2012 | Murata | G16H 10/40 705/2 |
| 2013/0277233 A1* | 10/2013 | Blythe | G16H 40/63 702/19 |
| 2014/0066892 A1* | 3/2014 | Keenan | A61B 5/14532 604/506 |
| 2014/0343530 A1 | 11/2014 | Bashan et al. | |
| 2014/0371682 A1* | 12/2014 | Bengtsson | G16H 20/17 604/189 |
| 2015/0045641 A1* | 2/2015 | Rule | A61B 5/150229 600/347 |
| 2016/0117481 A1 | 4/2016 | Booth et al. | |
| 2016/0256629 A1* | 9/2016 | Grosman | A61M 5/14244 |
| 2016/0342754 A1* | 11/2016 | Vettoretti | G16H 50/20 |
| 2017/0220751 A1* | 8/2017 | Davis | G06N 5/048 |
| 2017/0228518 A1* | 8/2017 | Booth | A61B 5/4839 |
| 2018/0277246 A1* | 9/2018 | Zhong | A61B 5/4833 |
| 2019/0147999 A1* | 5/2019 | Aradottir | G16H 50/20 604/504 |
| 2019/0180857 A1* | 6/2019 | Van Orden | G16H 50/20 |
| 2019/0272912 A1* | 9/2019 | Van Orden | G16H 50/30 |
| 2020/0227170 A1* | 7/2020 | Shvets | G16H 20/17 |
| 2020/0268968 A1* | 8/2020 | Steil | A61M 5/172 |
| 2021/0045640 A1* | 2/2021 | Poltorak | A61B 5/02055 |
| 2021/0146046 A1* | 5/2021 | Aradottir | G16H 20/17 |
| 2021/0327555 A1* | 10/2021 | Imanbayev | G16H 50/70 |

FOREIGN PATENT DOCUMENTS

| | | |
|---|---|---|
| JP | 2010-069065 A | 4/2010 |
| JP | 2011-064597 A | 3/2011 |
| JP | 2018-502341 A | 1/2018 |
| WO | WO 2009/137661 A1 | 11/2009 |
| WO | WO 2010/079554 A1 | 7/2010 |
| WO | WO 2010/089305 A1 | 8/2010 |
| WO | WO 2016/069475 A1 | 5/2016 |

OTHER PUBLICATIONS

PCT International Search Report and Written Opinion in International Application No. PCT/US2019/042974, dated Oct. 17, 2019, 13 pages.

\* cited by examiner

METHOD OF ADJUSTING MEDICATION DOSES

CROSS REFERENCE TO RELATED APPLICATIONS

The present application is the national stage entry of International Patent Application No. PCT/US2019/042974, filed Jul. 23, 2019, which claims priority to U.S. Provisional Patent Application No. 62/703,740, filed Jul. 26, 2018, and European Patent Application No. 19305621.5, filed May 15, 2019, the entire disclosures of which are incorporated herein by reference.

TECHNICAL FIELD

This specification relates to a method, apparatus and system for adjusting medicament doses. In particular, this specification relates to the automatic recommendation of medicament doses based on relaxed dosing regimen to a blood glucose measurement schedule.

BACKGROUND

Blood glucose monitoring forms an important part of the management of diabetes in diabetic patients. Regular blood glucose monitoring allows a diabetic patient to more effectively plan their medication regimen, meals and activities. One type of blood glucose measurement is a fasting blood glucose (FBG) measurement.

Blood glucose measurements are often paired with medicament doses, such as insulin doses, in order to monitor the effectiveness of the patient's medicament regimen. This allows for the patient's medicament regimen to be adjusted based in the measured effect of the medicament on the patient's blood glucose level.

However, in some circumstances diabetic patients may not check their blood glucose measurements on a regular basis, for example due to a lack of medical supplies, or simply due to forgetfulness. This can affect the provision of any treatment recommendations based on their blood glucose measurements.

SUMMARY

According to a first aspect, this specification describes a method of providing a medication dose adjustment using a computing device, the method comprising: receiving, by the computing device, an adjustment cycle time period; receiving, by the computing device, a threshold number of dose and blood glucose measurement pairs, the threshold number of dose and blood glucose measurement pairs being less than a total number of potential dose and blood glucose measurement pairs possible in the adjustment time cycle period; receiving, by the computing device, a dose and blood glucose measurement pair; determining, by the computing device, if a total number of dose and blood glucose measurement pairs received within a current adjustment cycle time period meets the threshold number, the current adjustment cycle time period depending on the received adjustment cycle time period; in response to a positive determination that the threshold number is met, determining, by the computing device, if a dose adjustment is required based on the dose and blood glucose measurement pairs received within an adjustment cycle time period; and outputting, by the computing device, the dose adjustment.

The current adjustment cycle time period may comprise a period of time prior to receiving the dose and blood glucose measurement pair equal to the adjustment cycle time period.

The current adjustment cycle time period comprises a period of time initiated by a predefined event. The predefined event may be an initial dose and blood glucose measurement pair.

The method may further comprise: determining, by the computing device, if the threshold number of dose and blood glucose measurement pair can be met within the current adjustment cycle time period; and in the event of a negative determination, initiating a new adjustment cycle time period.

Receiving, by the computing device, an adjustment cycle time period and receiving, by the computing device, a threshold number of dose and blood glucose measurement pairs may comprise scanning, by a scanner of the computing device, a settings token.

Receiving, by the computing device, the dose and blood glucose measurement pair may comprise: receiving, by the computing device, a dose indicator comprising a medicament dose value and a medicament dose time; receiving, by the computing device, a blood glucose measurement comprising a blood glucose level and a measurement time; determining, by the computing device, if the medicament dose time and the measurement time satisfy one or more predefined criteria; and in response to a positive determination, associating, by the computing device, the dose indicator and the blood glucose measurement to form the dose and blood glucose measurement pair.

Determining, by the computing device, if the medicament dose time and the measurement time satisfy one or more predefined criteria may comprise determining whether the dose time occurs within a first time range and the blood glucose measurement occurs within a second time range.

The method may further comprise: determining, by the computing device, if the received dose and blood glucose measurement pair comprises a medicament dose quantity that is outside a safety threshold; and in response to a positive determination, providing, by the computing device, a corrective warning.

The method may further comprise: determining, by the computing device, if the total number of dose and blood glucose measurement pairs is less than a predefined fraction of the total number of potential blood glucose measurements in the adjustment cycle time period; and in response to a positive determination, causing a warning to be issued. The predefined fraction may be up to one third of the total number of potential dose and blood glucose measurement pairs.

The method may further comprise: determining, by the computing device, if a blood glucose measurement is below a hypoglycaemic threshold; in response to a positive determination, determining, by the computing device, a dose adjustment based on the blood glucose measurement; and outputting, by the computing device, the dose adjustment. The method may further comprise: in response to a positive determination that the blood glucose measurement is below a hypoglycaemic threshold, initiating, by the computing device, a new current adjustment cycle time period.

According to a second aspect, this specification describes apparatus comprising: one or more processors; and a memory, the memory comprising instructions that, when executed by the one or more processors, causes the apparatus to perform any of the methods described herein.

According to a third aspect, this specification describes a computer program comprising computer readable instructions that, when executed by computer apparatus, cause the computing apparatus to perform any of the methods described herein.

BRIEF DESCRIPTION OF DRAWINGS

Example embodiments will now be described by way of non-limiting example with reference to the accompanying drawings, in which.

DETAILED DESCRIPTION

Overview

Figure 1:
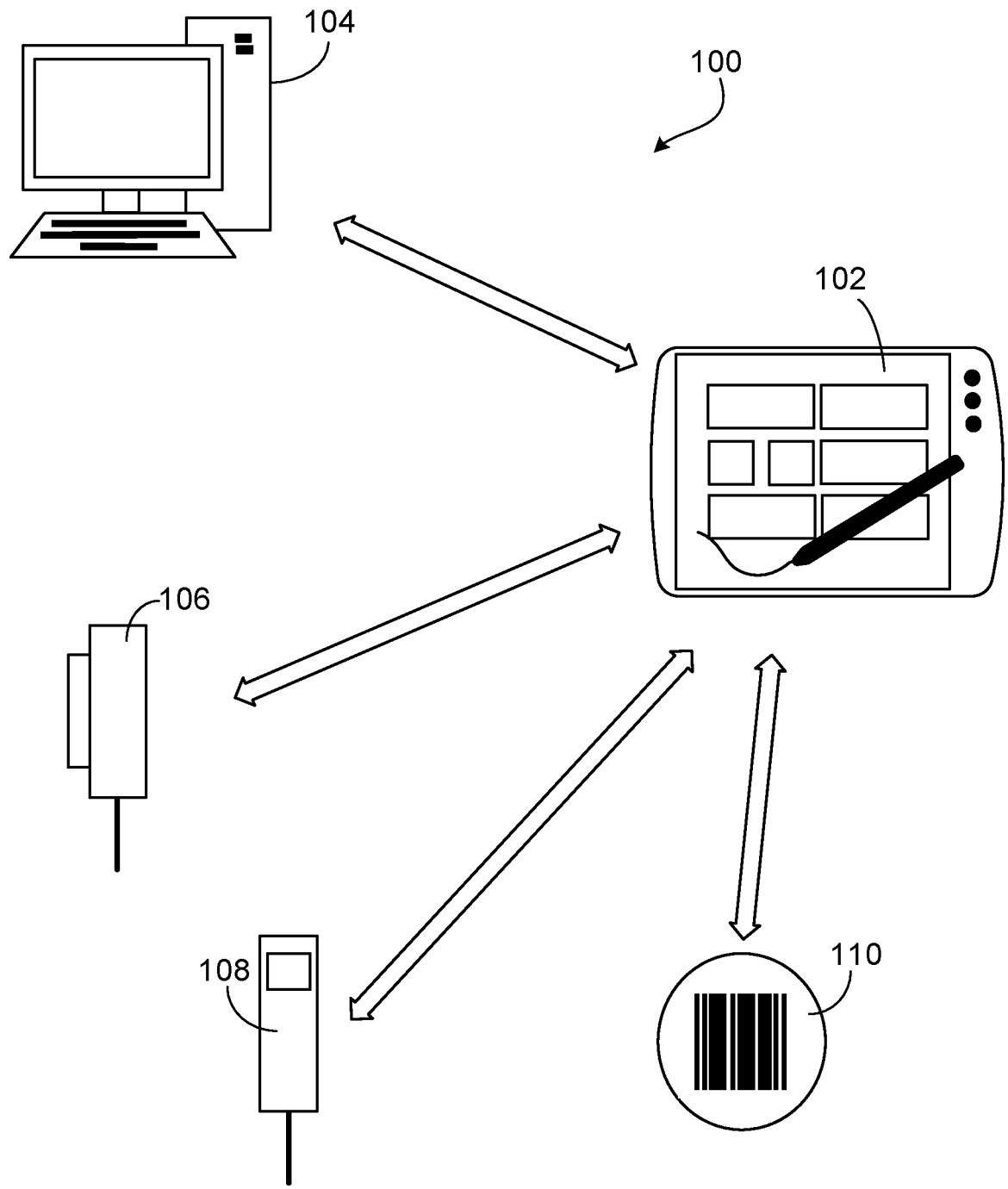
FIG. 1 shows an example of a system for managing medicament doses.

In some circumstances, it is not reasonable to expect that a diabetic patient will test their blood glucose level on a daily basis. There may be several potential limitations that prevent daily blood glucose testing, including, for example:
A shortage of blood glucose measurement supplies, such as lancets and test strips, perhaps due to excessive cost;
Illness;
Slips of the memory;
Fear of taking a dose, for example due to illness; and/or
Varying availability of Self-Monitoring Blood Glucose (SMBG) equipment.

In such situations, strict adherence to a blood glucose measurement regimen may prove difficult. Failing to adhere to the strict blood glucose measurement regimen, such as recording at least one blood glucose measurement a day for a predefined period of days (a "titration frequency"), may result in medication doses not being adjusted as frequently as necessary, as the patient has to complete a full blood glucose measurement cycle comprising a predefined number of consecutive days of blood glucose measurements before any dose adjustment is calculated. Such a measurement cycle can be referred to as a "fully compliant titration interval".

To address this limitation, a user device used for recording blood glucose measurements and provide medicament dose suggestions can be configured to provide medicament dose adjustments based on a relaxed dosing regimen. The relaxed regimen comprises pre-defined rules relating to how strictly a user should follow a user dose plan in order to successfully complete a titration interval. The pre-defined rules comprise a minimum required number of medicament dose and blood glucose measurement pairs (a "minimum acceptable adherence") that a user must gather over a span of time defined by a titration frequency in order to receive a potential dose adjustment. For example, the patient must gather two dose and blood glucose measurement pairs over three days, with two being the minimum acceptable adherence and three being the titration frequency. Measurement cycles using the relaxed adherence criteria can be referred to as a "relaxed adherence titration interval".

The titration frequency is defined as the minimum frequency of user dose adjustment. It can be selected by the user Health Care Professional (HCP). In some embodiments, it is defined as a number of days. For example, the titration frequency can be between one and seven days (inclusive), though other ranges are possible. The titration frequency is also referred to herein as the adjustment cycle time period and/or a dose adjustment frequency. If a user meets the minimum acceptable adherence within a period of time equal to a titration frequency, then a dose adjustment will be calculated.

A titration interval is defined as a period spanning at least the titration frequency during which the user keeps a medicament dose the same before the user blood glucose measurement values are evaluated and a potential suggested dose adjustment is made. A suggested dose is provided at the beginning of a titration interval based on data from the previous titration interval. If there is no previous titration interval, the suggested dose is the starting dose as defined in a user dose plan. A titration interval may be prematurely ended due to the occurrence of one or more pre-defined events. For example, the input of a hypoglycaemic blood glucose measurement may prematurely end the titration interval and result in a dose adjustment.

In this way, a customised, automated dose recommendation capability is provided to a user that can be tailored to the user tendencies. Dosing of medicament, such as insulin, is not required at every possible interval to effectuate a new dose recommendation. Depending on the dose adjustment frequency, the requirements for patient adherence (and, in some embodiments, potential warnings) are adjusted accordingly. By determining suggested doses in dependence on relaxed dosing regimen conditions, the frequency of dose adjustments for non-adherent users can be increased.

Generic System and Apparatus Diagram

FIG. 1 illustrates an example of a system 100 for managing medicament doses.

The system comprises a user computing device 102 that is configured to receive dose and blood glucose measurement pairs relating to a user. The user device is further configured to check whether received dose and blood glucose measurement pairs are consistent with a relaxed dosing regimen.

Figure 2:
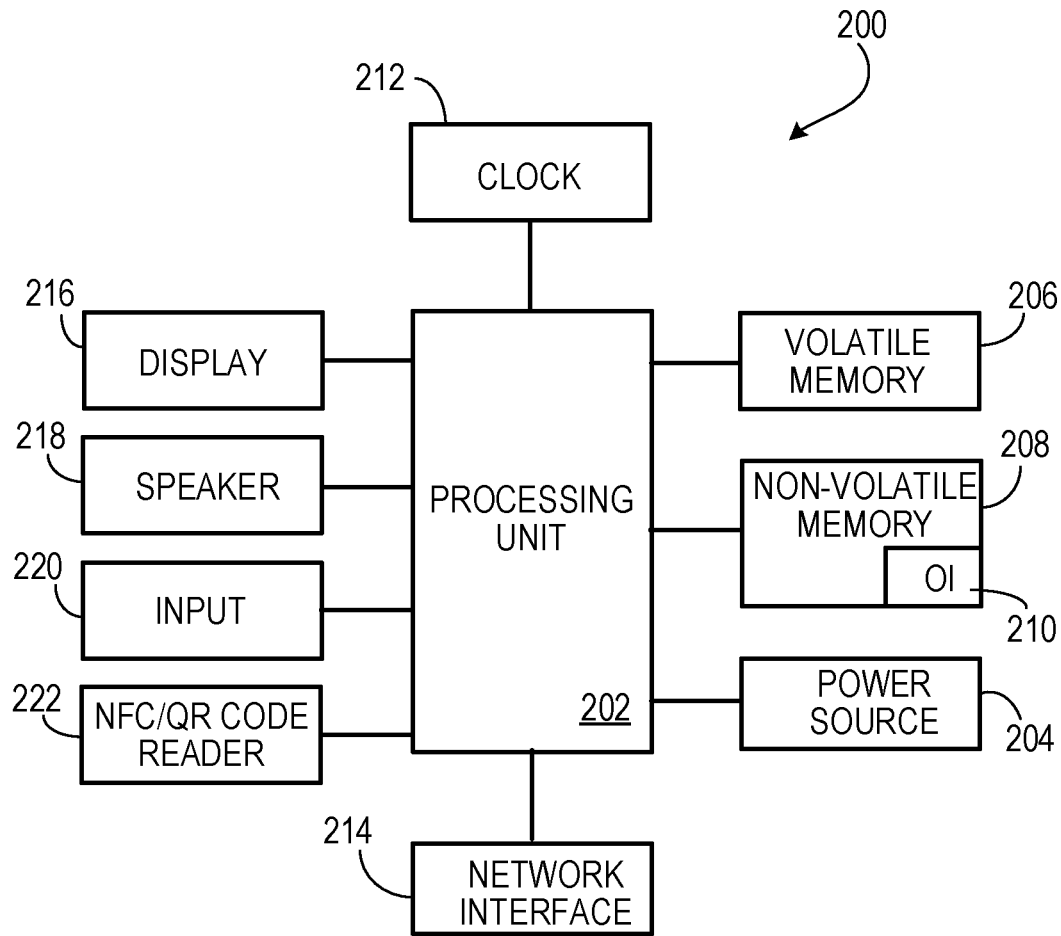
FIG. 2 shows a schematic example of an electronics system of an apparatus for managing medicament doses.

The user device 102 is configured to perform the method described in relation to FIG. 2. The method may be performed by an application running on the user device 102.

The user device may, for example, be any of: a mobile device, such as a mobile phone or tablet computer; a personal computer; a laptop; a personal digital assistant; a "smart" device; and/or a dedicated dose adjustment device.

The system may further comprise one or more external computing devices 104. The user device 102 may receive settings data relating to a relaxed adherence regimen, such as dose adjustment settings, from the external computing device via a network. The external computing device may be under the control of a user healthcare provider (HCP).

The system may further comprise one or more medicament administering devices 106. The medicament administering devices are operable to administer a medicament dose to the user. The administered medicament dose may be recorded by the medicament administering device 106 and sent to the user device 102. This administered dose data may be transferred to the user device 102 via a network. Alternatively or additionally, the administered dose data can be manually input to the user device 102, for example through a graphical user interface. The medicament administering device 106 may be in the form of an injection device.

The system may further comprise one or more blood glucose measurement devices 108. The blood glucose measurement devices 108 are operable to test the blood glucose levels of a user. The blood glucose level may be recorded by the blood glucose measurement device 108 and sent to the user device 102. This blood glucose measurement data may be transferred to the user device 102 via a network. Alternatively or additionally, the blood glucose measurement can manually input to the user device 102, for example through a graphical user interface.

In some embodiments, the system comprises one or more tokens 110. The tokens 110 can be scanned by the user device 102 to transfer settings data to the device. For example, a token 110 may comprise an RFID tag that can be scanned by an RFID reader in the user device 102. Alternatively, a token 110 may comprise a barcode that can be scanned by the user device 102.

FIG. 2 illustrates example electronic circuitry of the user device 102. The electronics system 200 of the user device 102 comprises the processor arrangement 202. The processor arrangement 202 and other hardware components may be connected via a system bus (not shown). Each hardware component may be connected to the system bus either directly or via an interface. A power supply 204 is arranged to provide power to the electronics system.

The processor arrangement 202 controls operation of the other hardware components of the electronics system 200. The processor arrangement 202 may be an integrated circuit of any kind. The processor arrangement 202 may for instance be a general purpose processor. It may be a single core device or a multiple core device. The processor arrangement 202 may be a central processing unit (CPU) or a general processing unit (GPU). Alternatively, it may be a more specialist unit, for instance a RISC processor or programmable hardware with embedded firmware. Multiple processors may be included. The processor arrangement 202 may be termed processing means.

The electronics system 200 comprises a working or volatile memory 206. The processor arrangement 202 may access the volatile memory 206 in order to process data and may control the storage of data in memory. The volatile memory 206 may be a RAM of any type, for example Static RAM (SRAM), Dynamic RAM (DRAM), or it may be Flash memory. Multiple volatile memories may be included, but are omitted from the Figure.

The electronics system comprises a non-volatile memory 208. The non-volatile memory 208 stores a set of operation instructions 210 for controlling the normal operation of the processor arrangement. The non-volatile memory 208 may be a memory of any kind such as a Read Only Memory (ROM), a Flash memory or a magnetic drive memory. Other non-volatile memories may be included, but are omitted from the Figure.

The processor arrangement 202 operates under the control of the operating instructions 210. The operating instructions 210 may comprise code (i.e. drivers) relating to the hardware components of the electronics system 200, as well as code relating to the basic operation of the user device. The operating instructions 210 may also cause activation of one or more software modules stored in the non-volatile memory 208. Generally speaking, the processor arrangement 202 executes one or more instructions of the operating instructions 210, which are stored permanently or semi-permanently in the non-volatile memory 208, using the volatile memory 206 temporarily to store data generated during execution of the operating instructions. The operating instructions may include computer readable instructions that, when executed by the processor arrangement 202, cause the user device to perform any of the methods described herein.

The processor arrangement 202, the volatile memory 206 and the non-volatile memory 208 may be provided as separate integrated circuit chips connected by an off-chip bus, or they may be provided on a single integrated circuit chip. The processor arrangement 202, the volatile memory 206 the non-volatile memory 208 may be provided as a microcontroller.

The electronics system 200 comprises a clock 212. The clock 212 may be a clock crystal, for example, a quartz crystal oscillator. The clock 212 may be a separate component to the processor arrangement 202 which is configured to provide a clock signal to the processor arrangement 202. The processor arrangement 202 may be configured to provide a real time clock based on the signal from the clock 212. Alternatively, the clock 212 may be a clock crystal which is provide on a single integrated circuit chip with the processor arrangement 202.

The electronics system 200 comprises one or more network interfaces 214. The network interfaces 214 facilitate the connection of the user device 102 to one or more computer networks and the bi-directional exchange of information between the user device 102 and other members of the networks. These networks may include the Internet, a Local Area Network, or any other network required by the user device to communicate with the data centre and/or contact centre. The network interfaces 214 comprise a network interface controller, such as an Ethernet adaptor, a Wi-Fi adaptor and/or a Bluetooth adaptor. The network interfaces 214 are associated with one or more network addresses for identifying the user device on the network. The one or more network addresses may be in the form of an IP address, a MAC address, and/or an IPX address. Other members of the network may include medical devices 106, 108 that are collecting user data.

In some embodiments, the processor arrangement 202 in the user may not be sufficiently powerful to perform one or more of the functions described herein. Instead, the processing arrangement 202 is configured to communicate via the network interface with an additional computer system that has more computing power available to it. The processor arrangement 202 can transmit data from the user device to the additional computer system, where it can be processed using the additional computing power of the additional computer system. The additional computer system can return the results of this processing back to the processor arrangement for further processing. The additional computing system can, for example, be a remote computer system, a distributed computer system, or part of a data centre.

The electronics system 200 further comprises a display 216. The display 216 can be operated by the processing arrangement 202 via a display driver to provide a graphical user interface to a user. The display 216 may in the form of an LCD screen. The display 216 may alternatively be in the form of an LED screen. The display 216 provides status information to the user relating to the user device 102. Examples of such status information include which mode the user device is in, a battery status, a memory status, a network connection status and/or whether an external power supply is connected. The display 216 may provide reminders to the user relating to the user's medication schedule. For example, a message may be provided on the display 216 stating when a user medication dose is scheduled to be administered.

The electronics system 200 may comprise a speaker 218. The speaker 218 is an example of an audio transducer. The speaker 218 can be operated to provide an audio output in the form of spoken word, or more generally any sound. The speaker 218 may provide audible feedback to the user relating to the use of the user device 102 and/or medical devices 106, 108. An example of this would be an audible indication that a medical device 106 was running low on medication contained in the device 106. In some embodiments, the speaker 218 may provide audible reminders to the user. For example, the speaker 218 may remind the user to take a scheduled dose of medication or record a blood glucose measurement.

The electronics system 200 further comprises one or more input interfaces 220. The input interfaces 220 allow a user to input data into the user device 102. Examples of input interfaces include a touch screen, a keyboard, a number pad, one or more dedicated buttons and/or a speech recognition engine.

The user device may, in some embodiments, comprise a reader 222, such as a near field communications transceiver. Near field communications tags, such as RFID tags, may then be read by the user device 102. The reader 222 may alternatively or additionally include a Quick Response (QR)-code reader, bar-code reader, or other optical code reader. The reader 222 may allow for the registration of medications that the user is using. For example, cartridges, auto-injectors (AIs), PFS and/or pills may be supplied with an RFID tag and/or optical code that can be read by the reader 222. This can provide information relating to the user's stock of medication, such as the amount of medication the user has been provided with or batch numbers of the medication. Furthermore, the reader 222 can be used to receive settings from the token 110.

Flow Diagram of Method

Figure 3:
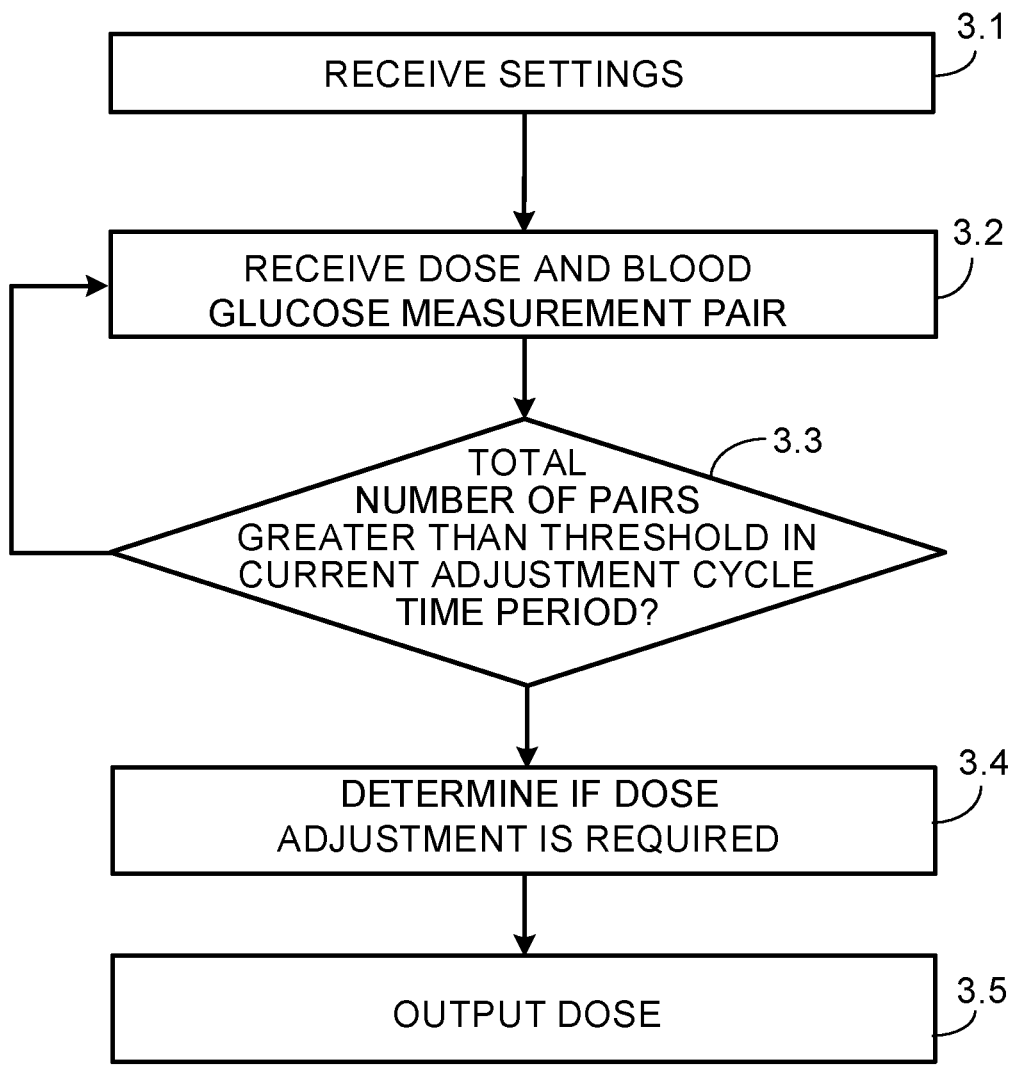
FIG. 3 shows a flow diagram of an example method of adjusting a medicament dose.

FIG. 3 shows a flow diagram of an example method of adjusting a medicament dose.

At operation 3.1, a user computing device 102 receives dose adjustment settings. The settings comprise a dose adjustment frequency comprising an adjustment cycle time period (i.e. titration interval), and a user adherence condition comprising the threshold number of dose and blood glucose measurement pairs. The user adherence condition defines a minimum acceptable adherence of between one dose and blood glucose measurement pair and the titration frequency. In other words, the user device 102 receives a minimum number of dose and blood glucose measurement pairs that a user should gather over a time span defined by an adjustment cycle time period in order to receive a potential dose adjustment.

For example, the user should gather two dose and blood glucose measurement pairs over three days, with two being the minimum acceptable adherence (i.e. threshold number of dose and blood glucose measurement pairs) and three being the titration frequency (i.e. adjustment cycle time period). In general, for a relaxed dosing regimen the minimum acceptable adherence will be less than the maximum number of dose and blood glucose measurement pairs possible in a titration frequency.

In some embodiments, the user computing device receives further dose adjustment settings. The further settings may comprise one or more of the following: FBG ranges and dose adjustments (fixed units and/or percent); a definition of a hypoglycaemia/hyperglycaemia level; a blood glucose calculation method (i.e. titration median or mean); a starting dose, for example between 0 and 500 units inclusive; a Usual Dose Time (UDT) for the user; and/or a maximum dose. In some embodiments, these further dose adjustment settings data are pre-loaded onto the user device. Alternatively, these further dose adjustment settings data may be received by the user device 102 in the same way as the settings data.

The settings may further comprise a predefined fraction of the total number of potential dose and blood glucose measurement pairs in the adjustment cycle time period. The predefined fraction can be used to issue a warning if the user does not meet that number of dose and blood glucose measurement pairs in an adjustment cycle time period, even if the number of pairs recorded is above the minimum adherence threshold. In some embodiments, warnings are only issued for titration frequencies of greater than four days. In some embodiments, the predefined fraction is up to one third of the total number of potential dose and blood glucose measurement pairs.

The user device 102 can receive settings through any suitable means. In some embodiments, the user device 102 receives the dose adjustment settings directly via graphical user interface on the user computing device 102. The user can manually input the dose adjustment settings using an input device associated with the user computing device 102.

In some embodiments, the dose adjustment settings are transmitted to the user device 102 from an external source, such as an external computing device 104, via a network. The external computing device 104 may be under the control of a healthcare professional.

In some embodiments, the user computing device 102 can be used to scan a token 110 from which it receives the dose adjustment settings. The token 110 may be provided by a healthcare professional, such as the user's doctor. The healthcare professional can configure the token 110 with the particular settings relevant to the user prior to the user scanning the token 110 with the user device 102. In some embodiments, the token comprises a Quick Response (QR) code that can be scanned by an imaging sensor on the user computing device 102. The QR code may, for example be printed on information provided to the user by the healthcare professional. In some embodiments, the token 110 comprises Radio-Frequency Identification (RFID) tag containing the dose adjustment settings that can be scanned by an RFID tag reader on the user device to receive the settings.

At operation 3.2, the user device receives a dose and blood glucose measurement pair. The blood glucose measurement may be a fasting blood glucose measurement, though other examples are possible.

The user device is configured to receive blood glucose measurement values, medicament dose values, and, in some embodiments, ad-hoc hypoglycaemic values. These values may be associated with one or more rules related to how and when these values may be entered, stored and/or edited. The received medicament dose (i.e. medicament dose indicator) may comprise a medicament dose value (i.e. the amount of medicament administered by the user) and a medicament dose time. Similarly, the blood glucose measurement may comprise a blood glucose level and a measurement time (i.e. the time that the measurement was taken by the user).

The dose and blood glucose pair may be manually input by the user via a graphical user interface on the user device. For example, the user device 102 may have a touch-screen display through which the user can input administered dose data and/or blood glucose measurement data. The user device 102 may comprise input means, such as a number pad or keyboard via which the user can input data.

In some embodiments, the user device 102 is configured to receive administered dose data from a medicament administering device 106 via a network interface. The user device 102 may be connected to the medicament administering device 106 via a network, such as a wireless network. The wireless network may for example be a Wi-Fi network and/or a Bluetooth™ network.

In some embodiments, the user device 102 is configured to receive blood glucose measurement data from a blood glucose measurement device 108 via a network interface. The user device 102 may be connected to the blood glucose measurement device 108 via a network, such as a wireless network. The wireless network may for example be a Wi-Fi network and/or a Bluetooth™ network.

The dose and blood glucose measure pair may, in some embodiments, be received together as a single input. In other embodiments, the medicament dose and blood glucose measurements are received by the computing device separately. The user may manually associate the medicament dose and blood glucose measurement to create the pair. The computing device may, in some embodiments, be configured to automatically associate the received medicament dose and blood glucose measurement to create a pair based on one or more pre-defined criteria.

For example, the predefined criteria may relate to the medicament dose time and the measurement time. For example, if the medicament dose time and the measurement time occur within a pre-defined range of times, then they may be associated to form as pair. If the medicament dose is validly received within a first time range and the blood glucose measurement is received within a second time range, then the medicament dose and blood glucose measurement are associated to form a pair. The second time range may depend on the first time range. For example, following a validly received medicament dose, as defined below, the second time range may be the time range in which a blood glucose measurement may be validly entered.

In some embodiments, a "Usual Dose Time" (UDT) may be provided for the user. The UDT defines time of day defined in the user dose plan around which the user should get a dose suggestion from the user device 102, take a dose of medicament, and record the dose on the user device 102. The UDT may be the same for each day. It may alternatively be variable between days. A UDT window is defined around the UDT, which defines a time window for each day during which the user can record a medicament dose. For example, the UDT window may comprise a time range centred on the UDT. A half-window time, "W", may be defined, such that the UDT window begins at a first time UDT-W and ends at a second time UDT+W. In some embodiments, W is equal to 3 hours, providing a 6 hour UDT window around the UDT.

In some embodiments, only one medicament dose is permitted to be recorded per day. Each dose value may be associated with a time at which the dose was administered. During a usual dose time window, the device may receive a dose value and a time at which the dose was administered. In some embodiments, only one dose value per usual dose window is permitted. In some embodiments, a dose value may only be permitted within a dose time window. For example, the dose administration time must be within a range of times to be considered a valid dose value. The range of times may be bounded at its earliest time by one or more of following events:

The start of the current usual dose time window;

A previous usual dose time minus a fraction of the dose suggestion window. In some embodiments, the fraction is a half of the dose window, for example 3 hours in a six hour dose window;

A previous blood glucose measurement time; and/or

A previous dose plan activation time.

The latest of these events can be used to define the earliest time of the range. The latest time of the range may be bounded by the present time (i.e. the time that the dose value is received).

The dose value is, in some embodiments, associated with one or more editing rules. The editing rules specify when and how the dose value may be edited. For example, the dose value may only be edited within a time window from the receipt of the dose value to one or more of: the end of the current usual dose time window; the time of a next blood glucose measurement; and/or the time of the next dose plan activation.

In some embodiments, only one blood glucose measurement is permitted per day. A blood glucose measurement may only be permitted within a measurement time window during a day. For example, the measurement time must be within a range of times to be considered a valid blood glucose measurement. The range of times may be bounded at its earliest time by one or more of following events:

The previous UDT+W time;

The end of the previous dose time window;

A previous medicament dose time;

A previous dose plan activation time; and/or

A rollover time for the current day.

The latest of these events can be used to define the earliest time of the range. The latest time of the range may be bounded by the present time (i.e. the time that the blood glucose measurement is received).

The blood glucose measurement is, in some embodiments, associated with one or more editing rules. The editing rules specify when and how the blood glucose measurement may be edited. For example, one or more of the following rules may be applied:

If the blood glucose measurement is hypoglycaemic, it cannot be edited by the user once confirmed; and/or If the blood glucose measurement is not hypoglycaemic, it can be edited within a pre-defined time period. The pre-defined time period may comprise the time period after receipt of the measurement until one or more of the following events occurs: the time the next dose vale is received; the end of the next usual dose time window (i.e. next UDT+W); and/or the rollover time for the current day. The earliest of these events may define the pre-defined time period.

A non-adherent time period is a time period in which the user fails to record a dose and blood glucose measurement pair with the user device. One or more of the following criteria may be used to determine a non-adherent time period: a missed blood glucose measurement; a missed medicament dose; and/or a medicament dose different from the suggested dose provided by the computing device.

A missed blood glucose measure is be determined to have occurred when no glucose measurement is received after the receipt of a medicament dose and the end of the next UDT window (i.e. between the dose on titration day (N−1) and the end of the UDT window on day N) and/or before the next medicament dose is received (i.e. the dose on day N).

A missed dose is determined to have occurred if no medicament dose for the current day has been input by the end of UDT window (i.e. UDT+W for day N is reached with no medicament dose being recorded for day N).

In some embodiments, a safety threshold is provided that indicates a safe range of medicament doses for the user. For example, it may comprise a maximum and or minimum safe dose for the user. If the received dose and blood glucose measurement pair comprises a medicament dose quantity that is outside a safety threshold, a corrective warning can be provided to the user. The corrective warning may comprise instructions on how to remedy the incorrect dose. The corrective warning may comprises an instruction to contact the user healthcare provider. In some embodiments, the corrective warning may also be transmitted to a user health care provider.

In some embodiments, the computing device can also receive one or more ad-hoc hypoglycaemic blood glucose measurements. A hypoglycaemic blood glucose measurement is a blood glucose reading recorded by the user that is at or below the hypoglycaemic threshold defined the user dose plan. The user may, in some embodiments, enter as many ad-hoc hypoglycaemic blood glucose measurements as they wish. Once received and confirmed, these may not be edited by the user.

At operation 3.3, the user device determines if the total number of dose and blood glucose measurement pairs meets the threshold in a current adjustment cycle time period.

The current adjustment cycle time period can be defined in a number of ways. In some embodiments, a "rolling" adjustment cycle time period is used. Alternatively, a "fixed" adjustment cycle time period can be used.

When in a rolling adjustment cycle time period setting, the computing device checks if the total number of dose and blood glucose measurement pairs received in a period of time prior to receiving the latest dose and blood glucose measurement pair equal to the adjustment cycle time period meets the threshold. In other words, the current adjustment cycle time period comprises the time period from an adjustment cycle time before the current time to the current time. In some embodiments, the rolling adjustment cycle time period does not begin until after a pre-defined time period (for example, a titration frequency) after the titration interval begins.

When in a fixed time adjustment cycle time period setting, a predefined event initiates the current adjustment cycle time period. For example, the receipt of an initial dose and blood glucose measurement pair may initiate a first current adjustment cycle time period. A dose adjustment is not performed until the fixed time adjustment cycle time period has elapsed.

In some embodiments using the fixed time adjustment cycle time period, the user device 102 determines if the threshold number of dose and blood glucose measurement pair can be met within the current adjustment cycle time period. If the threshold number cannot be met within the current adjustment cycle time period, a new adjustment cycle time period is initiated. For example, the titration frequency is five days, and the minimum adherence threshold is three pairs. After the start of the titration interval, a first pair is recorded over the second and third day. No pair is recorded over the third and fourth day. The user device determines that it is then impossible to meet the threshold number of three pairs within the current adjustment cycle time period, as it is only possible to record one more pair within the current adjustment cycle time period. A new adjustment cycle time period is therefore started.

In some embodiments, after the dose adjustment has been output, the computing device initiates a new adjustment cycle time period/titration interval. Due to the flexible adherence conditions, missed doses and/or missed blood glucose measurements do not result in the start of a new adjustment cycle time period/titration interval.

If a new dose plan is activated, the current titration interval may be ended and a new titration interval is started with the new dose plan. If a dose plan is activated while in a UDT window, a new titration interval may begin immediately. If a dose plan is activated outside a UDT window, a new titration interval is started on the next titration day after activation.

Examples of titration intervals are provided in more detail below with reference to FIGS. 4-7.

The user device may, in some embodiments, also determine the total number of dose and blood glucose measurement pairs is less than a predefined fraction of the total number of potential blood glucose measurements in the adjustment cycle time period; and in response to a positive determination, causing a warning to be issued.

At operation 3.4, the computing device determines if a dose adjustment is required based on the dose and blood glucose measurement pairs.

One of more of the pre-defined events can end a titration interval/current adjustment cycle time period and result in a dose adjustment. The successful completion of a titration interval is one such event. Blood glucose measurement values are gathered from the now-completed titration interval. The mean or titration median is used to derive a blood glucose value to look up the dose adjustment. Note that an adjustment of zero units is possible in some embodiments. In some embodiments, a hypoglycaemic blood glucose measurement may also end the titration interval. The hypoglycaemic blood glucose measurement itself is used to look up the dose adjustment. Multiple hypoglycaemic blood glucose measurements have a non-cumulative effect on the dose adjustment, with only the lowest value being used.

The dose adjustment may be determined based on a set of pre-defined rules. These rules may be received by the user device, for example from the user's healthcare professional, allowing the rules to be tailored for a specific user. The dose adjustment may be provided as number of units to increase/decrease the user medicament dose by. The dose adjustment may, in some circumstances, be zero units.

In some embodiments, the adjusted dose is calculated as a Dose Suggestion Units Adjustment. If the dose plan for particular blood glucose measurement calls for a unit adjustment (e.g. +2 U or −3 U), this adjustment is output via the user device 102 to the user. The adjustment is from the dose suggested at the start of the previous titration interval (i.e. the last dose suggestion).

In some embodiments, the adjusted dose is alternatively or additionally calculated as a Dose Suggestion Percent Adjustment. If the dose plan for the resulting blood glucose measurement calls for a percent adjustment (e.g. +10% or −20%), the adjustment is applied to the last dose suggestion. The dose may adjustment may be rounded down to the nearest unit. As an example illustration: 5.8 units is rounded to 5 units; 5.1 is rounded to 5 units; −5.1 is rounded to −6 Units; and/or −5.8 is rounded to −6 Units.

In some embodiments, a percentage dose adjustment always results in adjusting the dose suggestion by at least one unit. For example: if a last dose suggestion of 5 units is adjusted by +10%, the new dose suggestion is 6 units; if a last dose suggestion of 0 units is adjusted by 1%, the new dose suggestion is 1 units; and/or if a last dose suggestion of 5 units adjusted by −1%, the new dose suggestion is 4 units.

The suggested dose may not exceed the maximum dose set by the dose plan. For example, if the dose adjustment calculation indicates that the medicament dose should be adjusted to above the maximum dose set by the dose plan, the dose adjustment is capped to an adjustment that results in the maximum dose.

A dose plan may be provided with an expiration date. Upon reaching the expiration date of the dose plan, the user is blocked from using the user device 102 to obtain a dose adjustment. In some embodiments, and automated notification can be generated upon reaching the end of the dose plan. The automated notification can, for example, request the user to contact the user healthcare provider to renew the dose plan, and/or notify the user to visit the user healthcare provider.

At operation 3.5, the adjusted medicament dose is output. The dose may be output via a display on device. The user can then manually enter the dose into a medicament delivery device, such that the medicament delivery device will provide the adjusted dose when used by a user.

In some embodiments, the device may output the adjusted dose to a medicament delivery device via a network interface. For example, the adjusted dose may be transmitted over a wireless network, such as Wi-Fi or Bluetooth, from the device to the medicament delivery device. In response to receiving the adjusted dose, the medicament delivery device can automatically adjust dosage settings.

In some embodiments, if a dose adjustment is determined to be required and a gap in usage is encountered, a new dose recommendation is still made at the next possible UDT. For example, if a Minimum Acceptable Adherence of 5 pairs and Titration Frequency of 7 days is set:
- Activation on Monday morning. The titration interval starts.
- Pair 1—Dose on Monday night, FBG Tuesday morning.
- Pair 2—Dose on Tuesday night, FBG Wednesday morning.
- Pair 3—Dose on Wednesday night, FBG Thursday morning.
- Pair 4—Dose on Thursday night, FBG Friday morning.
- Pair 5—Dose on Friday night, FBG Saturday morning.
- Saturday night, open app within UDT, no dose adjustment since 7 days have not passed since the start of titration interval. No dose is taken.
- Sunday night, open app within UDT, no dose adjustment since 7 days have not passed since the start of titration interval. No dose is taken.
- No app usage for several weeks. The next time the app is opened within the UDT window, a new dose recommendation is made since 5 pairs were gathered over 7 days within the titration interval.

Figure 4:
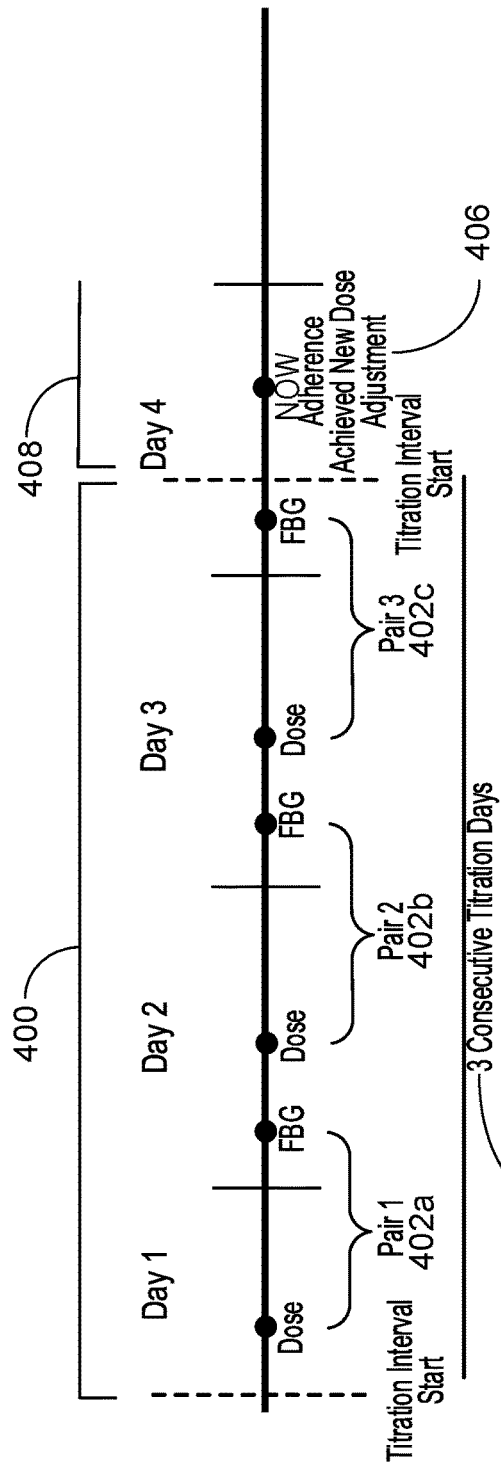
FIG. 4 shows an example of a fully compliant titration interval.

FIG. 4 shows an example of a fully compliant titration interval. In a fully compliant titration interval 400, one dose and blood glucose measurement pair 402 is recorded per day for a number of days equal to the titration frequency 404. In the example shown, the titration frequency is set to three days, so three dose and blood glucose measurement pairs 402a, 402b, 402c are collected to complete the titration interval. However the titration frequency 404 may be any suitable time period. Upon collection of the third dose and blood glucose measurement pair 402c, the user device determines if an adjustment to the medication dose is required and outputs an adjusted medication dose 406. A new titration interval is then started 408.

Figure 5:
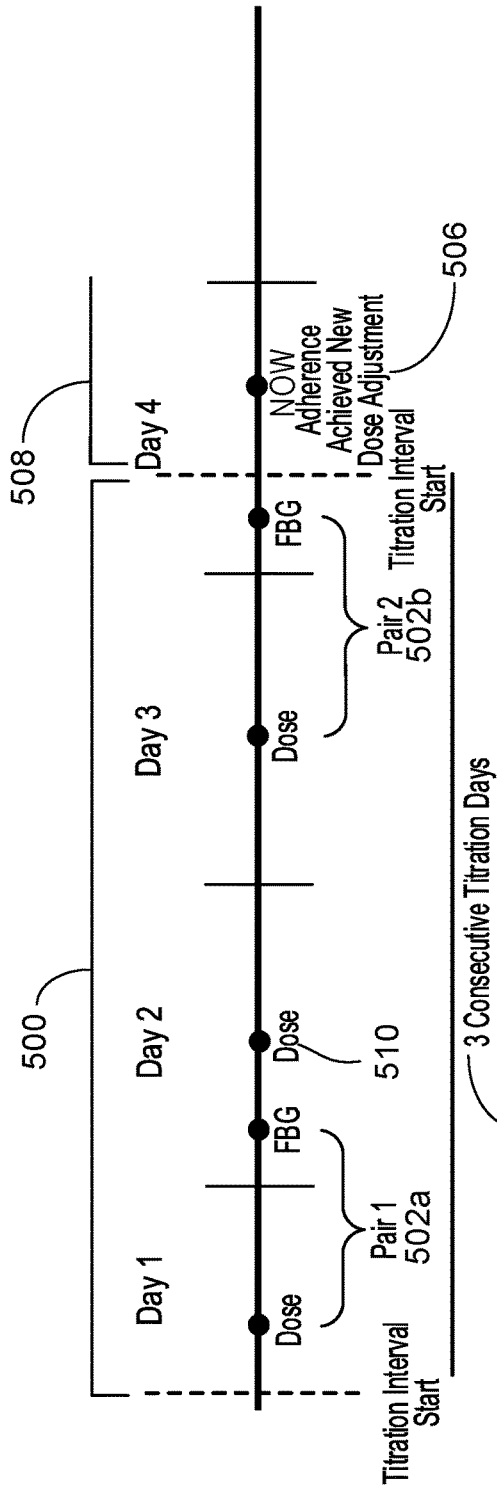
FIG. 5 shows an example of a relaxed compliance titration interval.

FIG. 5 shows an example of a relaxed dosing regimen titration interval 500. In this example, the titration frequency 504 is three days, and the minimum adherence threshold is two blood glucose measurements. However, the titration frequency 504 can be any suitable time period, and the minimum adherence threshold can be any number that is less than the maximum number of compliant pairs possible in the titration frequency.

Following the start of the titration interval 500, a first dose and blood glucose measurement pair 502a is recorded spanning the first and second days of the titration interval. A second dose 510 is recorded on the second day of the titration interval, but no corresponding blood glucose measurement is recorded with which it can be paired. A third dose is recorded on the third day of the titration interval. A second blood glucose measurement is subsequently recorded (in this example on day four of the titration interval), which is paired with the third dose to create a second dose and blood glucose measurement pair 502b. The minimum adherence threshold (in this case two pairs) has been met within a period of time equal to the titration frequency 504, so the computing device determines if a dose adjustment is required. The dose adjustment 506 is then output. A new titration interval 508 is started on day four. The titration interval 500 is therefore three days long.

In some embodiments, the titration interval 500 ends when the minimum adherence threshold is met. For example, if the second dose 510 in the example in FIG. 5 was followed by a blood glucose measurement with which it could be paired, the titration interval 500 would end on day two of the titration interval, without waiting for a period of time equal to the titration frequency 504 to elapse. A new titration interval 508 would therefore be started on day two.

Alternatively, in some embodiments, the titration interval 500 may only be ended after a period of time at least equal to the titration frequency 504 has elapsed. For example, even if the second dose 510 in the example in FIG. 5 was followed by a blood glucose measurement with which it could be paired, a dose adjustment 506 would not be provided until a period of time equal to the titration frequency 504 had elapsed (i.e. three days from the beginning of the titration interval).

Figure 6:
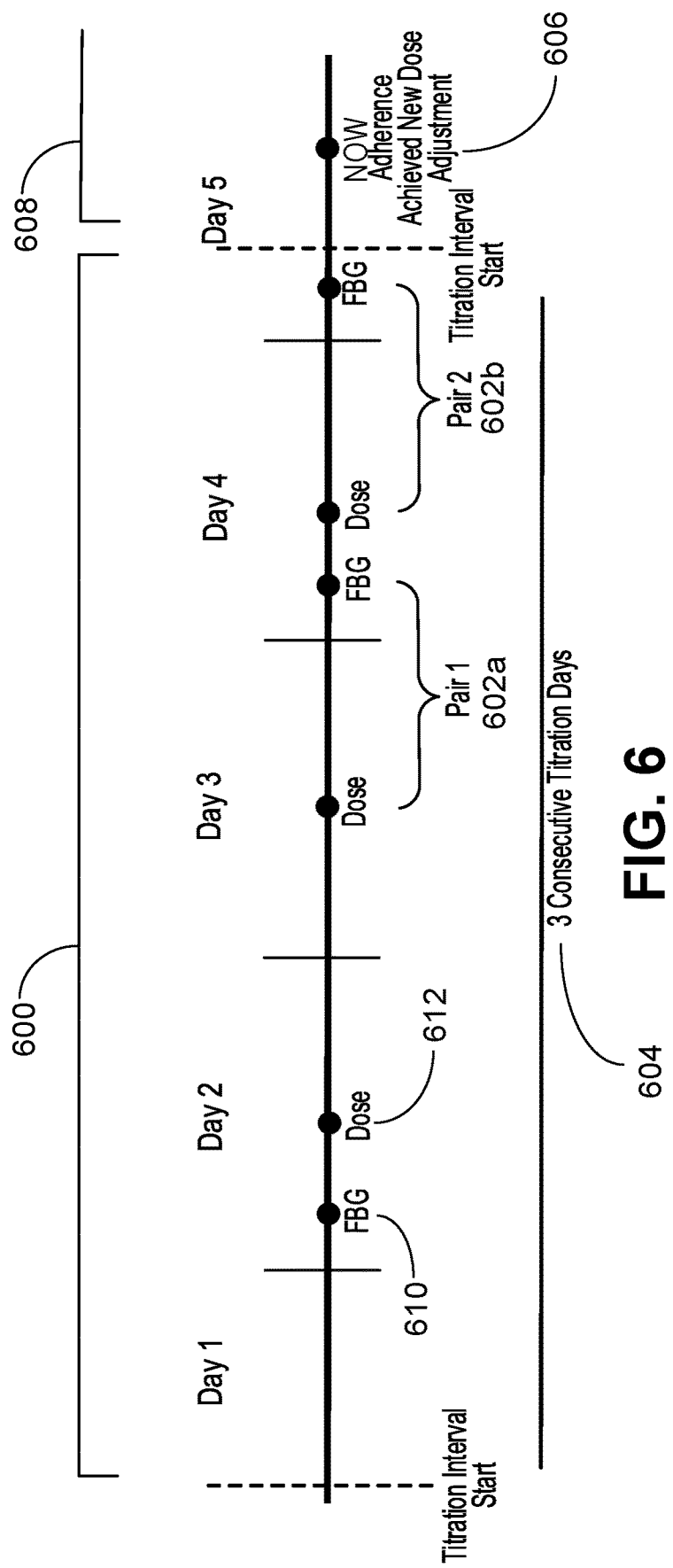
FIG. 6 shows a further example of a relaxed compliance titration interval.

FIG. 6 shows a further example of a relaxed dosing regimen titration interval 600. In this example, the titration frequency 604 is again three days, and the minimum adherence threshold is two blood glucose measurements. In this example, a rolling adjustment cycle time period is used.

Following the start of the titration interval a first blood glucose measurement 610 is received by the computing device on day two of the titration interval. However, there is no dose recorded with which it can be paired. A first medicament dose 612 is then recorded on day two at a time after the first blood glucose measurement 610. No blood glucose measurement is recorded that can be paired with the first dose 612.

Subsequently, a first adherent pair 602a is recorded over day three and day four of the titration interval. The user device 102 then checks if the minimum adherence threshold (in this case two pairs) has been met over a preceding number of days equal to the titration frequency 604 (in this example three days). In this example, as no previous pairs have been recorded, the minimum adherence threshold is not met. No dose adjustment is therefore performed on the fourth day.

A second adherent pair 602b is recorded over day three and day four of the titration interval 600. The user device 102 checks if the minimum adherence threshold (in this case two pairs) has been met over a preceding number of days equal to the titration frequency 604 (in this example three days). In this example, as the first adherent pair 602a had been recorded within that time period, the minimum adherence threshold is met. A dose adjustment 606 is therefore determined on the fifth day. A new titration interval 608 is then started.

Figure 7:
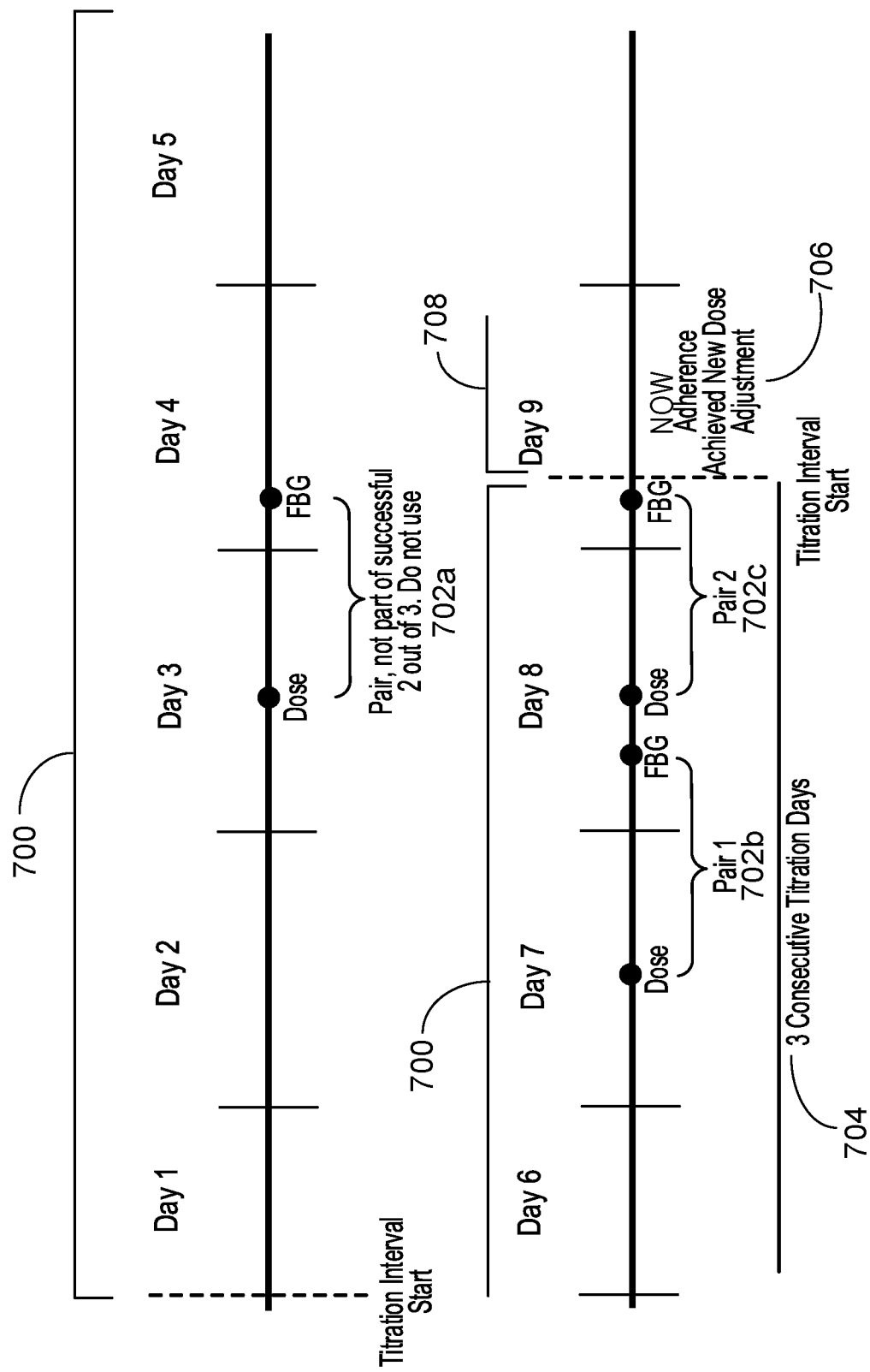
FIG. 7 shows another example of a relaxed compliance titration interval.

FIG. 7 shows another example of a relaxed compliance titration interval. In this example, the titration frequency 704 is again three days, and the minimum adherence threshold is two blood glucose measurements.

Following the start of the titration interval 700, a first dose and blood glucose measurement pair 702a is recorded spanning the third and fourth days of the titration interval 700. The user device 102 then checks if the minimum adherence threshold (in this case two pairs) has been met over a preceding number of days equal to the titration frequency 704 (in this example three days). In this example, as no previous pairs have been recorded, the minimum adherence threshold is not met. No dose adjustment is therefore performed on the fourth day.

A second dose and blood glucose measurement pair 702b is recorded over the seventh and eighth days of the titration interval 700. The user device 102 then checks if the minimum adherence threshold has been met over a preceding number of days equal to the titration frequency 704. In this example, as there are three non-adherent days between the first pair 702a and the second pair 702b being recorded, the minimum adherence threshold is not met. No dose adjustment is therefore performed on the eighth day.

A third adherent pair 702c is recorded over day eight and day nine of the titration interval 700. The user device 102 checks if the minimum adherence threshold has been met over a preceding number of days equal to the titration frequency 704. In this example, as the second adherent pair 702b had been recorded within that time period, the minimum adherence threshold is met. A dose adjustment 706 is therefore determined on the ninth day. A new titration interval 708 is then started.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codeable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin. Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-w carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. A method of providing a medication dose adjustment using a computing device, the method comprising:
receiving, by the computing device, data identifying an adjustment cycle duration;
receiving, by the computing device, data identifying a threshold number of dose and blood glucose measurement pairs, the threshold number being a positive integer value that is greater than one and less than a total number of potential dose and blood glucose measurement pairs possible in an adjustment cycle having a duration defined by the adjustment cycle duration; and after receiving, by the computing device, the data identifying the adjustment cycle duration and the threshold number:

receiving, by the computing device and during a current adjustment cycle, a plurality of dose and blood glucose measurement pairs;

determining, by the computing device, if a total number of dose and blood glucose measurement pairs that have been received within the current adjustment cycle meets the threshold number, wherein the current adjustment cycle has a duration defined by the adjustment cycle duration;

in response to a positive determination that the threshold number is met, determining, by the computing device, if a dose adjustment is required based on the plurality of dose and blood glucose measurement pairs received within the current adjustment cycle; and outputting, by the computing device, the dose adjustment, comprising:

transmitting data characterizing the dose adjustment to a medicament delivery device; and automatically controlling the medicament delivery device to cause the medicament delivery device to dispense an amount of medication defined based the dose adjustment.

2. The method of claim 1, wherein the current adjustment cycle comprises an interval of time that: (i) immediately precedes a time point when a most recent dose and blood glucose measurement pair was received, and (ii) has a duration equal to the adjustment cycle duration.

3. The method of claim 1, wherein the current adjustment cycle comprises an interval of time that: (i) immediately follows a time point when an initiating event occurred, and (ii) has a duration equal to the adjustment cycle duration.

4. The method of claim 3, wherein the initiating event comprises receiving a first dose and blood glucose measurement pair of the plurality of dose and blood glucose measurement pairs.

5. The method of claim 1, wherein receiving, by the computing device, data identifying an adjustment cycle duration and receiving, by the computing device, data identifying a threshold number of dose and blood glucose measurement pairs comprises scanning, by a scanner of the computing device, a settings token.

6. The method of claim 1, wherein for one or more of the plurality of dose and blood glucose measurement pairs received during the current adjustment cycle, receiving, by the computing device, the dose and blood glucose measurement pair comprises:

receiving, by the computing device, a dose indicator comprising a medicament dose value and a medicament dose time;

receiving, by the computing device, a blood glucose measurement comprising a blood glucose level and a measurement time;

determining, by the computing device, if the medicament dose time and the measurement time satisfy one or more predefined criteria; and in response to a positive determination, associating, by the computing device, the dose indicator and the blood glucose measurement to form the dose and blood glucose measurement pair.

7. The method of claim 6, wherein determining, by the computing device, if the medicament dose time and the measurement time satisfy one or more predefined criteria comprises determining whether the dose time occurs within a first time range and the blood glucose measurement occurs within a second time range.

8. The method of claim 1, the method further comprising, for one or more of the plurality of dose and blood glucose measurement pairs received during the current adjustment cycle:

determining, by the computing device, if the dose and blood glucose measurement pair comprises a medicament dose quantity that is outside a safety threshold; and in response to a positive determination, providing, by the computing device, a corrective warning.

9. The method of claim 1, the method further comprising:

determining, by the computing device, if the total number of dose and blood glucose measurement pairs that have been received within the current adjustment time cycle is less than a predefined fraction of the total number of potential blood glucose measurements possible in an adjustment cycle having a duration defined by the adjustment cycle duration; and in response to a positive determination, causing a warning to be issued.

10. The method of claim 9, wherein the predefined fraction is up to one third of the total number of potential dose and blood glucose measurement pairs possible in an adjustment cycle having a duration defined by the adjustment cycle duration.

11. The method of claim 1, further comprising:

determining, by the computing device, if a blood glucose measurement is below a hypoglycemic threshold;

in response to a positive determination, determining, by the computing device, an additional dose adjustment based on the blood glucose measurement; and outputting, by the computing device, the additional dose adjustment.

12. The method of claim 11, further comprising:

in response to the positive determination that the blood glucose measurement is below a hypoglycemic threshold, initiating, by the computing device, a new adjustment cycle.

13. A system comprising:

a computing device; and one or more memory devices, the one or more memory devices comprising instructions that, when executed by the computing device, cause the computing device to perform operations comprising:

receiving, by the computing device, data identifying an adjustment cycle duration;

receiving, by the computing device, data identifying a threshold number of dose and blood glucose measurement pairs, the threshold number being a positive integer value that is greater than one and less than a total number of potential dose and blood glucose measurement pairs possible in an adjustment cycle having a duration defined by the adjustment cycle duration; and after receiving, by the computing device, the data identifying the adjustment cycle duration and the threshold number:

receiving, by the computing device and during a current adjustment cycle, a plurality of dose and blood glucose measurement pairs;

determining, by the computing device, if a total number of dose and blood glucose measurement pairs that have been received within the current adjustment cycle meets the threshold number, wherein the current adjustment cycle has a duration defined by the adjustment cycle duration;

in response to a positive determination that the threshold number is met, determining, by the computing device, if a dose adjustment is required based on the plurality of dose and blood glucose measurement pairs received within the current adjustment cycle; and outputting, by the computing device, the dose adjustment, comprising:
transmitting data characterizing the dose adjustment to a medicament delivery device; and
automatically controlling the medicament delivery device to cause the medicament delivery device to dispense an amount of medication defined based the dose adjustment.

14. One or more non-transitory computer-readable storage media storing instructions that, when executed by a computing device, cause the computing device to perform operations comprising:

receiving, by the computing device, data identifying an adjustment cycle duration;

receiving, by the computing device, data identifying a threshold number of dose and blood glucose measurement pairs, the threshold number being a positive integer value that is greater than one and less than a total number of potential dose and blood glucose measurement pairs possible in an adjustment cycle having a duration defined by the adjustment cycle duration; and after receiving, by the computing device, the data identifying the adjustment cycle duration and the threshold number:

receiving, by the computing device and during a current adjustment cycle, a plurality of dose and blood glucose measurement pairs;

determining, by the computing device, if a total number of dose and blood glucose measurement pairs that have been received within the current adjustment cycle meets the threshold number, wherein the current adjustment cycle has a duration defined by the adjustment cycle duration;

in response to a positive determination that the threshold number is met, determining, by the computing device, if a dose adjustment is required based on the plurality of dose and blood glucose measurement pairs received within the current adjustment cycle; and outputting, by the computing device, the dose adjustment, comprising:
transmitting data characterizing the dose adjustment to a medicament delivery device; and
automatically controlling the medicament delivery device to cause the medicament delivery device to dispense an amount of medication defined based the dose adjustment.

15. The one or more non-transitory computer storage media of claim 14, wherein the current adjustment cycle comprises an interval of time that: (i) immediately precedes a time point when a most recent dose and blood glucose measurement pair was received, and (ii) has a duration equal to the adjustment cycle duration.

16. The one or more non-transitory computer storage media of claim 14, wherein the current adjustment cycle comprises an interval of time that: (i) immediately follows a time point when an initiating event occurred, and (ii) has a duration equal to the adjustment cycle duration.

17. The one or more non-transitory computer storage media of claim 16, wherein the initiating event comprises receiving a first dose and blood glucose measurement pair of the plurality of dose and blood glucose measurement pairs.

18. The one or more non-transitory computer storage media of claim 14, wherein receiving, by the computing device, data identifying an adjustment cycle duration and receiving, by the computing device, data identifying a threshold number of dose and blood glucose measurement pairs comprises scanning, by a scanner of the computing device, a settings token.

19. The one or more non-transitory computer storage media of claim 14, wherein for one or more of the plurality of dose and blood glucose measurement pairs received during the current adjustment cycle, receiving, by the computing device, the dose and blood glucose measurement pair comprises:

receiving, by the computing device, a dose indicator comprising a medicament dose value and a medicament dose time;

receiving, by the computing device, a blood glucose measurement comprising a blood glucose level and a measurement time;

determining, by the computing device, if the medicament dose time and the measurement time satisfy one or more predefined criteria; and in response to a positive determination, associating, by the computing device, the dose indicator and the blood glucose measurement to form the dose and blood glucose measurement pair.

20. The one or more non-transitory computer storage media of claim 19, wherein determining, by the computing device, if the medicament dose time and the measurement time satisfy one or more predefined criteria comprises determining whether the dose time occurs within a first time range and the blood glucose measurement occurs within a second time range.

* * * * *

UNITED STATES PATENT AND TRADEMARK OFFICE
CERTIFICATE OF CORRECTION

| | | |
|---|---|---|
| PATENT NO. | : 11,967,407 B2 | Page 1 of 1 |
| APPLICATION NO. | : 17/262595 | |
| DATED | : April 23, 2024 | |
| INVENTOR(S) | : Timothy Moloy | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 623 days.

Signed and Sealed this
Eighth Day of October, 2024

Katherine Kelly Vidal
*Director of the United States Patent and Trademark Office*